US00PP30932P2

(12) United States Plant Patent
Egger

(10) Patent No.: US PP30,932 P2
(45) Date of Patent: Oct. 8, 2019

(54) ***HEUCHERA* PLANT NAMED 'TNHEUGA'**

(50) Latin Name: ***Heuchera* hybrid**
Varietal Denomination: TNHEUGA

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,138

(22) Filed: Oct. 1, 2018

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by a large habit with leaves that are purple and ruffled, great performance in the landscape or as a container plant, great winter foliage color and hardiness, a high crown count, and excellent vigor.

1 Drawing Sheet

Botanical denomination: *Heuchera* hybrid.
Variety designation: 'TNHEUGA'.

BACKGROUND OF THE INVENTION

The present invention relates to a new and distinct cultivar of *Heuchera* given the cultivar name of 'TNHEUGA'. *Heuchera* is in the family Saxifragaceae. *Heuchera* 'TNHEUGA' originated as a controlled cross using *Heuchera* B107-4, a proprietary, unnamed plant as the seed parent, and *Heuchera* B121-3, a proprietary, unnamed plant as the pollen parent. The trademark designation is 'Grande™ Amethyst'.

Compared to the seed parent B107-4, the new cultivar has leaves that have a stronger purple-black color, flowers on shorter inflorescences, and a larger habit.

Compared to the pollen parent B121-3, the new cultivar has leaves that have a stronger purple color.

Compared to *Heuchera* 'FOREVER™ Purple', U.S. Plant Pat. No. 26,358, the new cultivar has a purple-black foliage rather than rose to light plum.

Compared to *Heuchera* 'Velvet Night', an unpatented plant, the new cultivar has larger leaves and habit, with leaves a darker purple and black.

This new *Heuchera* is uniquely distinguished by:

1. large habit with leaves that are purple and ruffled,
2. a great landscape or container plant,
3. great winter foliage color and hardiness,
4. a high crown count, and
5. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 1 shows two-year-old plants of *Heuchera* 'TNHEUGA' growing in the trial beds in September in Canby, Oreg.

FIG. 2 shows the new cultivar as an eight-month-old plant growing in a one gallon container, grown in a warm greenhouse in July in Canby, Oreg.

DETAILED PLANT DESCRIPTION

The following is a detailed description of the new *Heuchera* cultivar based on observations taken in mid-October of a two-year-old specimen grown in trail beds outside in full sun in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* $5^{th}$ edition, 2007.

Plant:

*Form.*—Basal rosette, herbaceous perennial.
*Hardiness.*—USDA Zone 4 to 9.
*Size.*—2-year-old plants grow to 65 cm wide and 47 cm tall.
*Number of crowns.*—18.
*Habit.*—Mounding.
*Vigor.*—Excellent.

Leaf:

*Type.*—Simple.
*Arrangement.*—Rosette.
*Shape.*—Broadly ovate.
*Lobing/division.*—7 to 8 shallow lobes, shallow secondary lobes.

*Venation*.—Palmate.
*Margins*.—Crenate, fluted.
*Apex*.—Mucronulate.
*Base*.—Cordate.
*Blade size*.—Grows to 16 cm long and 13.8 cm wide.
*Surface texture*.—Glandular on both sides.
*Rugosity*.—Absent.
*Petiole description*.—Grows to 19 cm long and 5.1 mm wide, glandular hairs, Purple N79A.
*Leaf color*.—Topside, closest to Greyed Purple N187A with main palmate veins Greyed Purple 187A, secondary veins Black 203C, bottom side closest to Purple N79A with veins N79B.

Inflorescence:
*Size*.—Grows to 5.5 cm wide and 23.5 cm long.
*Type*.—Thyrse.
*Number of flowers per thyrse*.—About 100.
*Number of thyrse*.—17.
*Peduncle*.—Grows to 31 cm long and 4 mm wide at base, between Purple N79 and Purple N77, glandular hairs.
*Pedicel*.—Range in size includes 12-17 mm, with glandular hairs, between Purple N79 and Purple N77.
*Attitude*.—Upwards to semi-upwards.
*Bloom period*.—Late April to November in Canby, Oreg.

Flower bud:
*Size*.—4 mm wide and 5 mm long.
*Description*.—Glandular puberulent, ovoid, down facing.
*Color*.—Red Purple 58A on bottom ⅓ to Red Purple 62B on middle ⅔ to Red Purple 59A on top.

Flower:
*Type*.—Perfect.
*Shape*.—Campanulate.
*Attitude*.—Outwards to semi-downwards.
*Size*.—8 mm long and 5 mm wide.
*Corolla description*.—5 petals, 3 mm long and 1 mm wide, margins entire, tip acute, glabrous on both sides, Red Purple 62D on both sides.
*Calyx description*.—Campanulate, 5 mm long and 4 mm wide, with 5 lobes divided ½ way to the base, each 2 mm wide and 3 mm long, glandular on top and bottom, tip obtuse, margin entire; color inside Purple 76B, outside Red Purple 64A on bottom ⅓ blending to Red Purple 65B in middle ⅔ to Purple N79 B on tips.
*Stamen description*.—5 in number, filaments 3 mm long, White NN155B, anthers 0.4 mm, Greyed Orange 177B; pollen Yellow Orange 17D.
*Pistil description*.—1, 2-beaked, 8 mm long and 0.5 mm wide, ovary 3 mm long and 1.8 mm wide, Red Purple 59D, style 5 mm long, Purple 75C.
*Fragrance*.—None.
*Lastingness*.—Each thyrse blooms for about 3 weeks on the plant.

Fruit:
*Type*.—Two-beaked ovoid capsule.
*Fertility*.—Low.
*Color*.—Greyed Brown 199C.

Seed:
*Shape*.—Linear.
*Size*.—1 mm long.
*Color*.—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

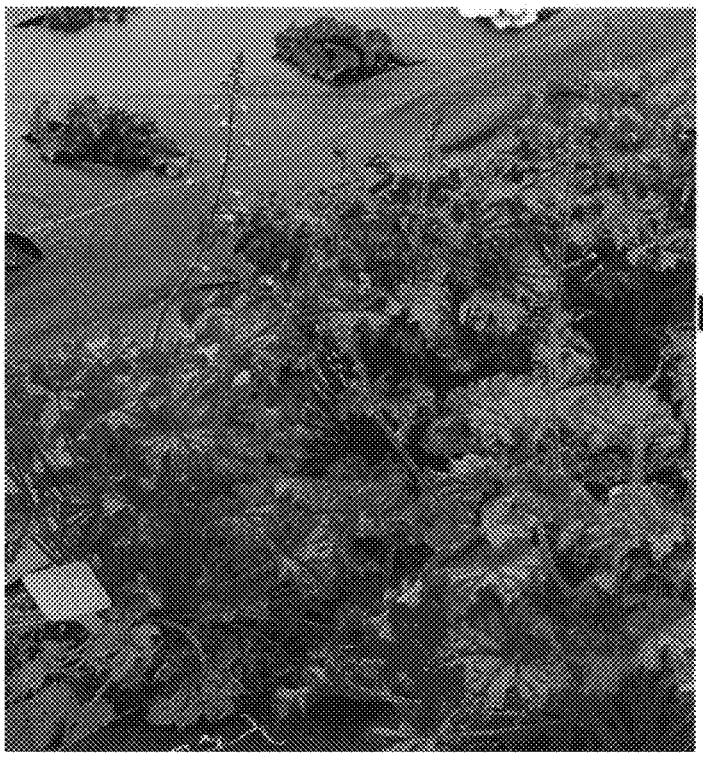
FIG. 1 left
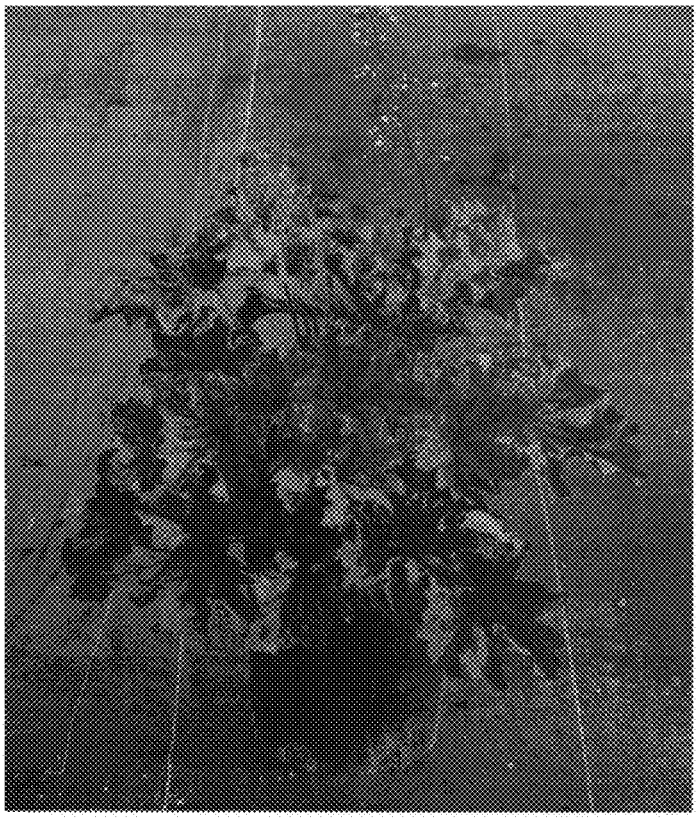
FIG. 2 left